(12) United States Patent
Nagy

(10) Patent No.: US 7,949,192 B2
(45) Date of Patent: May 24, 2011

(54) TECHNIQUES FOR CONVERTING ANALOG MEDICAL VIDEO TO DIGITAL OBJECTS

(75) Inventor: Paul Nagy, Ellicott City, MD (US)

(73) Assignee: University of Maryland, Baltimore, Baltimore, MD (US)

(*) Notice: Subject to any disclaimer, the term of this patent is extended or adjusted under 35 U.S.C. 154(b) by 1024 days.

(21) Appl. No.: 11/746,035

(22) Filed: May 8, 2007

(65) Prior Publication Data
US 2008/0123915 A1 May 29, 2008

Related U.S. Application Data

(60) Provisional application No. 60/799,295, filed on May 10, 2006.

(51) Int. Cl.
*G06K 9/72* (2006.01)
*G06F 17/30* (2006.01)

(52) U.S. Cl. .......................... 382/229; 707/762

(58) Field of Classification Search .................. None
See application file for complete search history.

(56) References Cited

U.S. PATENT DOCUMENTS

| | | | | |
|---|---|---|---|---|
| 5,950,207 | A * | 9/1999 | Mortimore et al. ................ | 1/1 |
| 2002/0080392 | A1* | 6/2002 | Parvulescu et al. .......... | 358/1.15 |
| 2004/0059756 | A1* | 3/2004 | Mochizuki .................... | 707/201 |
| 2004/0136602 | A1* | 7/2004 | Nagaraj et al. ................ | 382/240 |
| 2005/0131558 | A1* | 6/2005 | Braithwaite et al. ............ | 700/94 |
| 2006/0149601 | A1* | 7/2006 | Langhofer et al. ................ | 705/3 |
| 2008/0114481 | A1* | 5/2008 | Braithwaite et al. ............ | 700/94 |
| 2008/0123915 | A1* | 5/2008 | Nagy ............................ | 382/128 |

OTHER PUBLICATIONS

NEMA, Digital Imaging and Communication in Medicine (DICOM) Part 1: Introduction and Overview, /dicom/2004.htm1/04_01PU.PDF, Jan. 1, 2004, Publisher: National Electrical Manufacturers Association, Published in: Rosslyn, VA, USA and Internet:medical.nema.org.

* cited by examiner

*Primary Examiner* — Bhavesh M Mehta
*Assistant Examiner* — Tahmina Ansari
(74) *Attorney, Agent, or Firm* — Evans & Molinelli PLLC; Eugene Molinelli

(57) ABSTRACT

Techniques for converting analog medical video data to digital objects include receiving a digital video signal. The signal is produced by converting an analog video signal from playing a legacy analog medical video medium on an appropriate analog video player. Without human intervention, a first portion of a video frame of the digital video signal is determined where characters are imaged onto the analog medical video by the legacy system. The first portion of the video frame is processed in a video optical character recognition process to generate first character data. Non-video descriptive data associated with the analog medical video data is determined based on the first character data. Digital video data based on the digital video signal is stored in association with the non-video descriptive data. These techniques allow one or more extensive analog medical video libraries to be converted quickly and at low cost in human labor.

20 Claims, 5 Drawing Sheets

300 VIDEO FRAME SEQUENCE FROM LEGACY SYSTEM

310a VIDEO FRAME IMAGE
XQ123 120295 11:11:01.1  312a

310b VIDEO FRAME IMAGE
XQ123 120295 11:11:01.2  312b

310c VIDEO FRAME IMAGE
XQ123 120295 11:11:01.3  312c

310d VIDEO FRAME IMAGE
312d

310e VIDEO FRAME IMAGE
312e

310f VIDEO FRAME IMAGE
XQ123 120295 11:18:52.1  312f

310g VIDEO FRAME IMAGE
XQ123 120295 11:18:52.3  312g

310h VIDEO FRAME IMAGE
XQ123 120295 11:18:52.4  312h

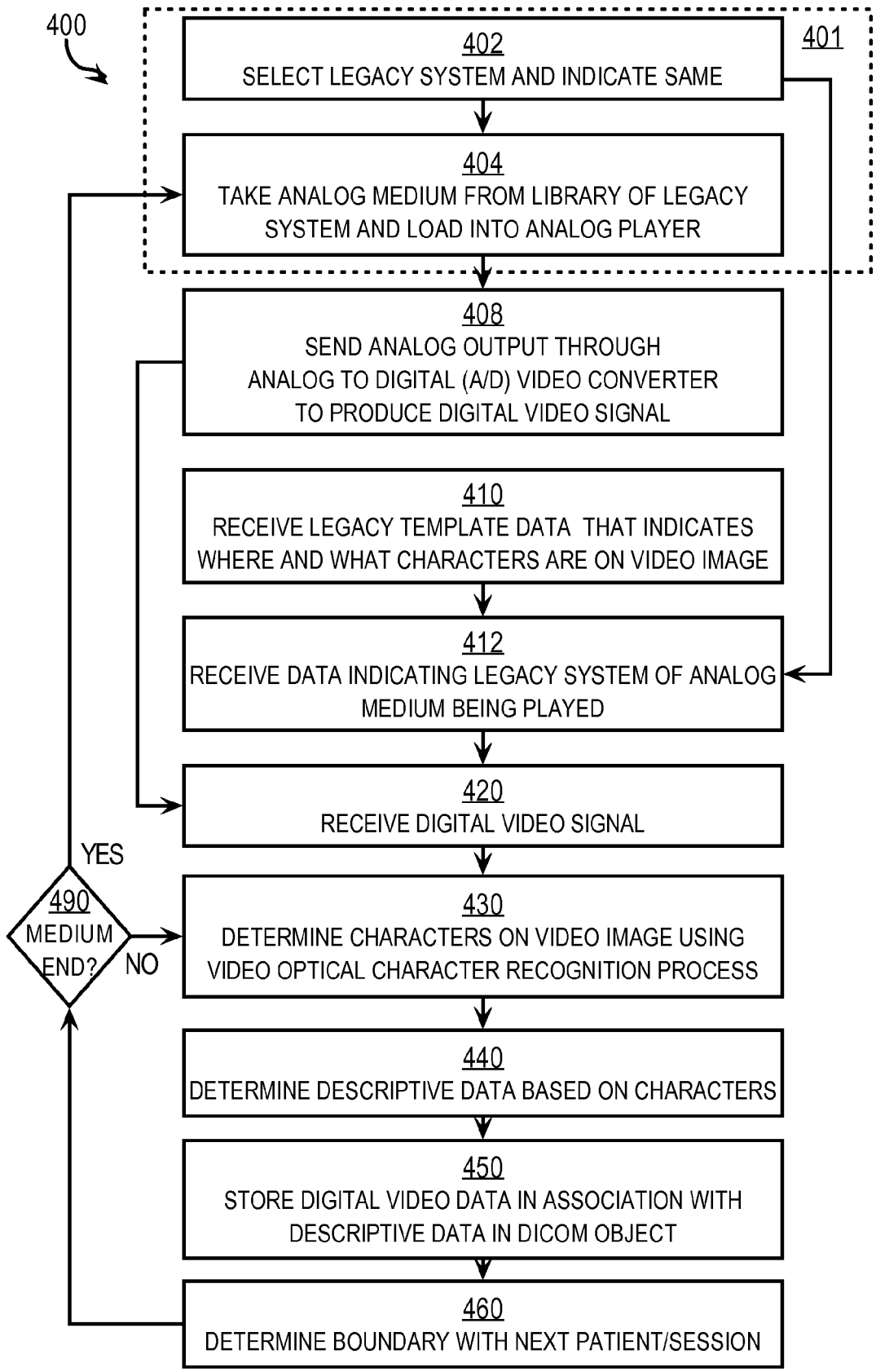

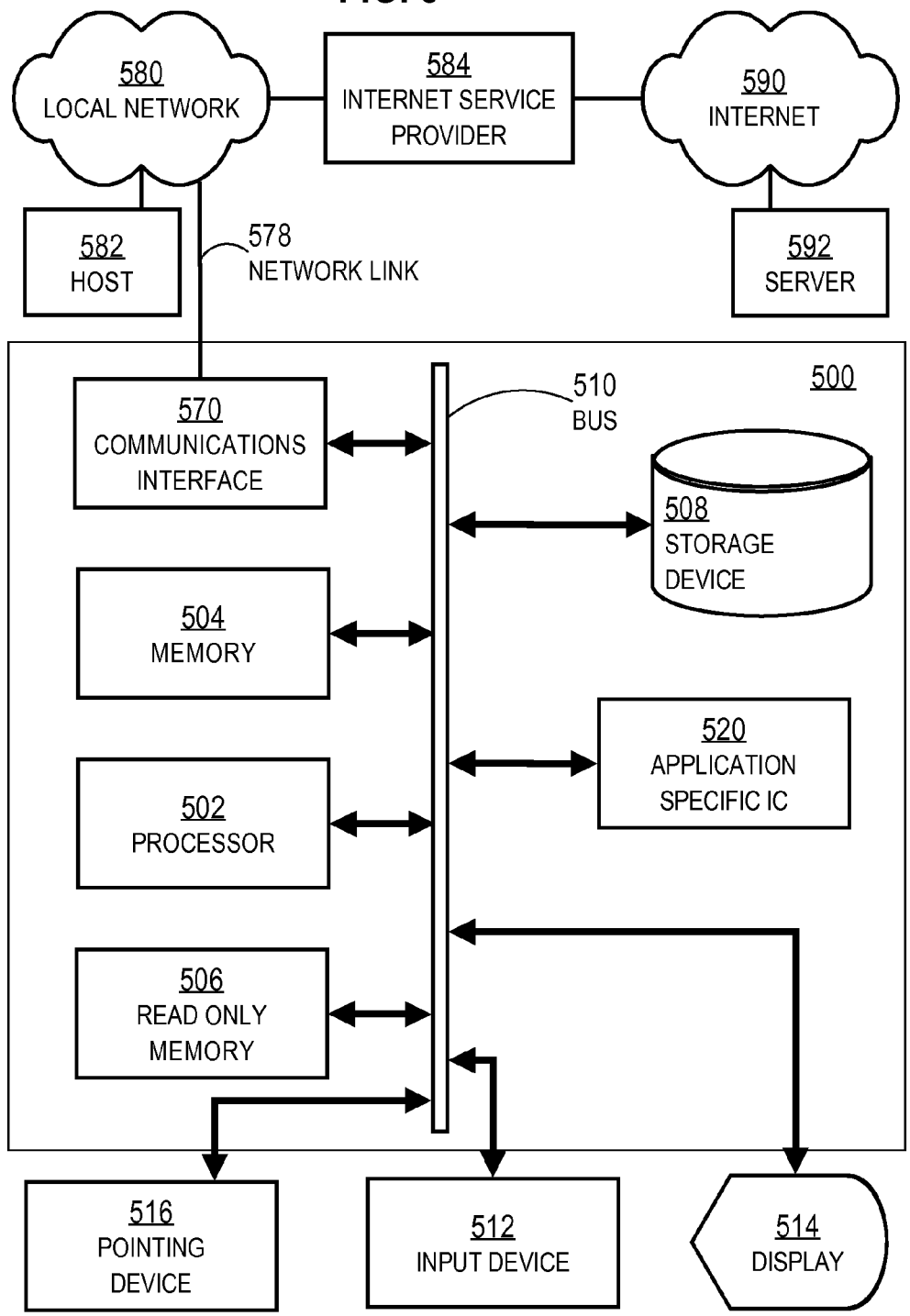

TECHNIQUES FOR CONVERTING ANALOG MEDICAL VIDEO TO DIGITAL OBJECTS

CROSS-REFERENCE TO RELATED APPLICATIONS

This application claims benefit of Provisional Appln. 60/799,295, filed May 10, 2006, under 35 U.S.C. §119(e).

BACKGROUND OF THE INVENTION

1. Field of the Invention

The present invention relates to converting analog medical video data to a digital object that associates descriptive data with the video, and, in particular, to forming Digital Imaging and Communications in Medicine (DICOM) objects from analog medical video data in a legacy data collection system.

2. Description of the Related Art

Medical care facilities collect video data in association with diagnostic and interventional radiological procedures, including fluorescence images of relative transmission and computer aided tomography (CAT) scan images based on Roentgen rays (X-rays), and echograms based on ultrasound. To associate each video clip with the patient and procedure for which the images were collected, characters were included in the recorded images that identified the patient-imaging session combination (called herein a patient-session identifier). Thus a human viewer of the video, such as a doctor could be assured that a particular video being viewed applied to a particular case under consideration.

Also associated with the video data is other information about the imaging session on the patient, such as the patient name or other identifier, the patient demographic data, e.g., age, height, weight, vital signs, family history, personal history, the imaging system identifier and maintenance history, the procedure itself, including study data when the imaging was performed as part of a study. This other descriptive data is stored separately from the video. For example, the non-video descriptive data was stored in journal entries or forms in a paper record, but more often as binary data on a computer storage medium in various files, sometimes within a database system.

These video data are archived as a record of the procedure, as a record of the patient's condition at the time of the procedure, and a baseline of patient condition to monitor the progression of a disease or a healing treatment. Several minutes to hours of such data is collected at a single medical facility for each of hundreds to thousands of patients per year, for many years.

In the past, the most efficient storage for such data has been as analog video data. Digital storage would require many terabytes of storage (a byte is about eight binary digits, called bits, a megabyte is a million bytes, and a terabyte is $10^{12}$ bytes—a million megabytes). Media such as hard magnetic disks for such data had limited capacity and were expensive. Vast numbers of such disks were required for digital storage. Analog formats could store more hours of data per medium and more cheaply. Many different such formats have been utilized from Beta-format video tapes, to standard VHS format video stapes, to proprietary formats defined for particular data collection systems. The analog data drives a television display using one of several worldwide standards, including PAL in Europe and NTSC in the United States. Several patient-session video clips are stored on a particular medium, typically a video tape, and the media are collected in libraries held at or for the benefit of each medical facility.

A variety of legacy and emerging systems have been used to collect video imaging data for patients, including, among others, systems from MERGE HEALTHCARE™ of Milwaukee, Wis.; Impax Master Patient Index (MPI) of AGFA HEALTHCARE™ of Mortsel, Belgium; Horizon Cardiology Echo of MCKESSON ALIPORT™ of Alpharetta, Ga.; Radiance Picture Archiving and Communication Systems (PACS) DEJARNETTE RESEARCH SYSTEMS, INC.™, of Towson, Md.; NAI DiCOM box CA+ Cine to DICOM of AMPRONIX INCORPORATED™, Irvine, Calif.; PACS systems of VEPRO™ of Hahn, Germany; CapturePRO systems of PEGASUS IMAGING CORPORATION™ of Tampa, Fla.; and Video Acquisition Workstation (VAW) of RAYPAX™ of Seoul, Korea.

When an archived video is to be reviewed for any reason, the appropriate volume of the medium must be identified, typically in a list or digital database, retrieved from the library, which can take several minutes if stored on site to several days if stored off site. Furthermore, a suitable player must be identified and located, the medium volume must be inserted, and the tape played forward until the correct clip is positioned in the viewer. There are costs associated with all these steps, not the least of which is the doctor's time in waiting for the appropriate clip to be positioned in the player after the data is requested. A significant cost to the patient's health and the doctor's inefficiency is the delay from the time that a need for the clip is identified until the proper medium volume is provided. Other costs include the librarian's salary, the salary of any other operators or technicians involved, the storage space for the media, the transportation costs between library and viewer, and the cost of maintaining the viewer, sometimes different viewers for different imaging systems. Such costs can often exceed a hundred thousand dollars a year.

Current digital storage techniques, such as hard magnetic drives and optical media such as DVDs, are now capable of efficiently storing such volumes of video data. An advantage of digital storage is that digital video data can now be stored in association with patient and procedure data related to the video data on the same storage medium. Data structures that combine multimedia data, images, sound, video, character and numeric data have been developed. Some are flexible enough to define their own fields. Object-oriented data bases define data objects that include not only data of different types, but also methods that are used for receiving input data, storing it, and retrieving it on request.

An object-oriented data format that has been adopted at many medical facilities is the Digital Imaging and Communications in Medicine (DICOM) system. DICOM is well known and widely used in the art of medical data and is available from the National Electrical Manufacturers Association (NEMA) of Rossyln, Va. Documentation of the DICOM standards is available at the time of this writing at subdomain dicom at domain nema at top level domain org as a Hypertext Markup Language (HTML) document ps3set.cfm in directory stds. The entire contents of ps3set.cfm are hereby incorporated by reference as if fully set forth herein.

There are benefits to converting the analog medical video data to digital data for storage in digital objects in association with other patient and procedure data, such as in DICOM objects. For example, the video and associated descriptive data can be retrieved over a network as soon as a need for it is identified, without intervention or costs of a human librarian or transporter, or the costs of one or more legacy analog video players, or the cost of time to advance a video tape. High capacity network digital storage is all that is required, and that is available reliably and cheaply as a commodity in current markets. The data can be kept indefinitely in a retrievable form independent of video players, even for the lifetime of a patient (many decades).

Unfortunately there are substantial obstacles in converting the analog data to digital form. Current systems involve a human operator playing each tape, determining the beginning and end of a clip associated with a single patient-imaging session, visually identifying the particular patient-imaging session based on the characters shown on the image, and retrieving data related to that patient-imaging session from one or more other digital files or databases. Then the portion of the tape must be played through an analog to digital converter and stored with the data from the database. Each legacy system would consume tens of thousands of hours of operator time (years of salary) to process all the video clips. Also, because the work is tedious and not related to a particular critical need of the patient whose data is being converted, the operator is prone to lose attention and to generate errors. Therefore the costs of the errors or checks to catch and correct errors would also be incurred. Again, these conversion costs can be expected to exceed a hundred thousand dollars a year for several years.

Based on the foregoing description, there is a clear need for techniques to convert large amounts of analog medical video data to digital objects that do not suffer the disadvantages of prior approaches. In particular, there is a need for techniques to convert analog medical video data to digital objects that involve very little human involvement.

The past approaches described in this section could be pursued, but are not necessarily approaches that have been previously conceived or pursued. Therefore, unless otherwise indicated herein, the approaches described in this section are not to be considered prior art to the claims in this application merely due to the presence of these approaches in this background section.

SUMMARY OF THE INVENTION

Techniques are provided for converting analog medical video data to digital objects. According to one set of embodiments, a method includes receiving a digital video signal produced by converting an analog video signal received in response to playing a recording of analog medical video collected for a legacy system on an analog video player compatible with the legacy system. Without human intervention, a first portion of a video frame of the digital video signal is determined where characters are imaged onto the analog medical video by the legacy system. The first portion of the video frame is processed in a video optical character recognition process to generate first character code data. Also without human intervention, non-video descriptive data associated with the analog medical video data is determined based on the first character code data. Still without human intervention, digital video data based on the digital video signal is stored in association with the non-video descriptive data, such as in a DICOM object.

In other sets of embodiments, a computer-readable medium, an apparatus and a system perform one or more steps of the above method.

BRIEF DESCRIPTION OF THE DRAWINGS

The present invention is illustrated by way of example, and not by way of limitation, in the figures of the accompanying drawings and in which like reference numerals refer to similar elements and in which:

FIG. 4 is a flow diagram that illustrates at a high level a method for converting analog medical video to combined digital data objects, according to an embodiment; and FIG. 5 is a block diagram that illustrates an example computer system upon which an embodiment of the invention may be implemented.

DETAILED DESCRIPTION

Techniques are described for converting analog medical video data to digital objects. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are descried below in the context of converting X-ray video clips to DICOM objects. However, the invention is not limited to this context. In other embodiments, the same or other data, such as ultrasound, laparoscopy, endoscopy, colonoscopy, interventional radiology and other video data are converted to the same or other digital objects, such as one or more digital database objects or files independent of a particular database.

1. Equipment Components

Figure 1:
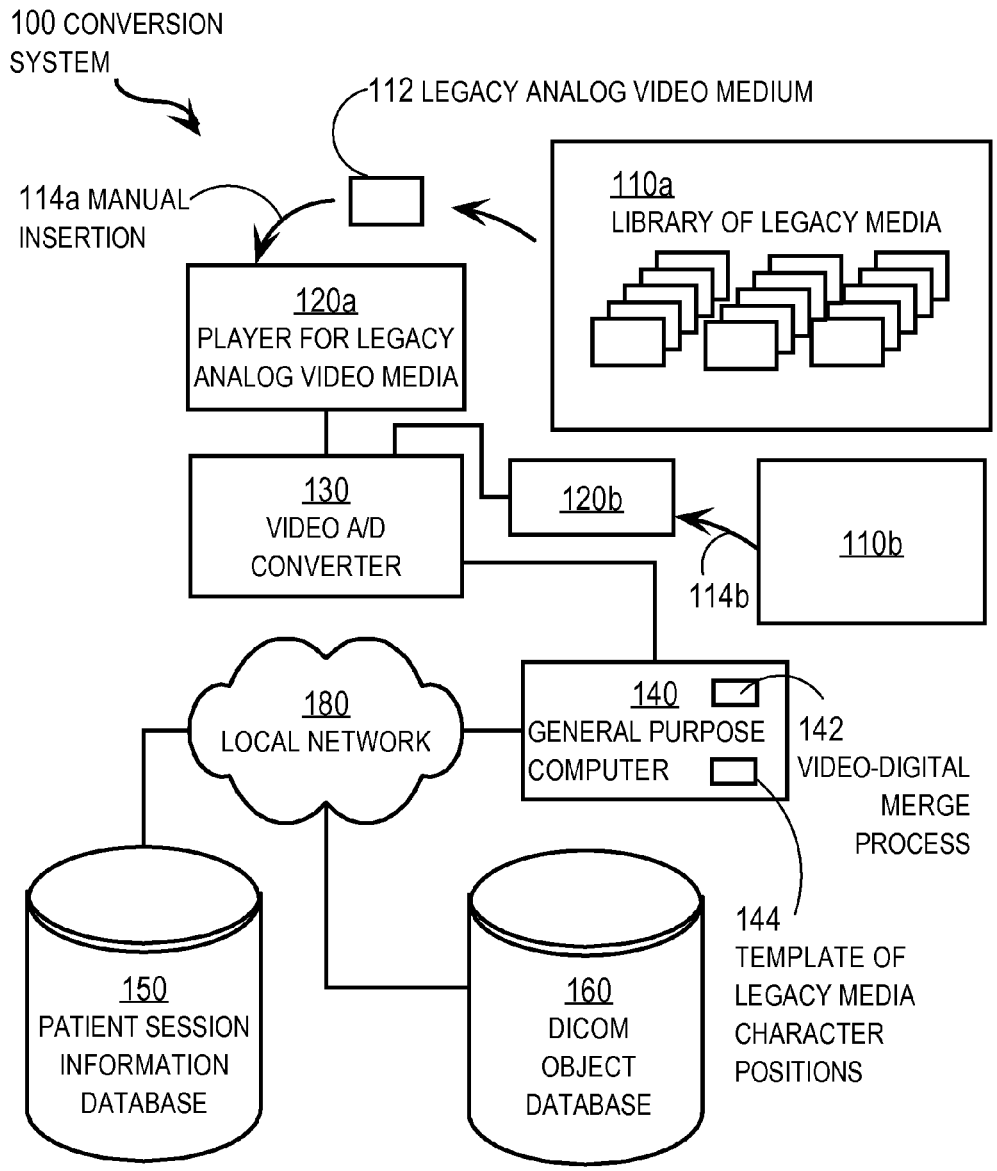
FIG. 1 is a block diagram that illustrates a system for converting analog video data to digital objects with video and non-video data, according to an embodiment of the invention.

FIG. 1 is a block diagram that illustrates a system 100 for converting analog video data to digital objects with video and non-video data, according to an embodiment of the invention. System 100 includes a first library 110a and a second library 110b (collectively referenced hereinafter as analog libraries 110) of legacy analog video media, such as legacy analog video medium 112. System 100 also includes an analog media payer for each of the legacy libraries, e.g., analog player 120a and analog player 120b (collectively referenced hereinafter as analog players 120) for media from library 110a and library 110b, respectively. System 100 also includes video analog to digital (A/D) converter 130 and computer 140. System 100 includes patient-encounter information database 150 and DICOM object database 160 connected to computer 140 through local network 180.

A library 110 is any archive of analog media, whether on site at the medical facility or offsite. The legacy analog video medium 112 is any medium used in a library and is considered uniform for all media in one library 110. The medium 112 indicates a combination of both a physical medium, such as tape or disk, and the format for data on the physical medium. Different media are stored in different libraries. For example, the media in library 110b are different than the media in library 110a, although both libraries may be located in the same room or facility.

An analog player 120 is any device that is capable of producing an analog video signal from the legacy analog video medium. In some embodiments, the analog player 120 is part of a legacy system. In some embodiments, the analog player 120 is a common electronic device, such as a VHS player for NTSC video data that is compatible with the media produced by a legacy system. In an illustrated embodiment, analog players 120 are capable of playing legacy analog video medium at faster than real time, where real time is a play speed that renders realistic motion of objects represented in the stream of images that constitute the video data.

The video A/D converter 130 is any device that converts an analog signal to a digital signal. For example, digital video recorders (DVRs), such as TiVo devices from TIVO of Alviso, Calif., are configured to receive analog video for NTSC and record it in a digital format. Any digital format may be output by A/D converter 130. Sample digital video formats include Motion Pictures Engineering Group (MPEG) video format, MPEG II format, MPEG IV format, all well known in the art. MPEG is a digital format that permits compression to various degrees, including lossless compression. In the illustrated embodiment, video A/D converter 130 is capable of converting analog video at faster than real time so that data output by the player 120 is not lost during conversion.

The patient-encounter information database 150 is any database with information to be associated with the video data. For example, database 150 includes information such as patient identifier, encounter identifier, procedure type, date of procedure, start time of procedure, duration of procedure, imaging device identifier, and identifier for imaging device operator. In an example embodiment, the patient-encounter information database 150 is a Radiology Information System (RIS). RIS includes patient demographics data and study demographics data, if any. In some embodiments, database 150 is simply a collection of one or more files with data of interest. In some embodiments, database 150 is a sophisticated database, such as a commercial relational database with data files and a server for responding to standard query language (SQL) commands.

The DICOM object database 160 is a database of DICOM objects that each combine photographic images and video clips with non-image character and numeric data. In some embodiments, database 160 is simply a collection of one or more files with DICOM objects. In some embodiments, database 160 is a sophisticated database, such as a commercial relational database with a server for responding to standard query language (SQL) commands.

The computer 140 and digital data are described in more detail in a later section. According to some embodiments of the invention, computer 140 includes a video-digital merge process 142 and legacy template data 144. The video-digital merge process 142 associates non-video digital data with digital video clips produced by the video A/D converter 130. The template data 144 associates different legacy systems with different areas on an image from a video clip where images of characters are included. In some embodiments, the template data also indicates the type of information (called herein a context or an attribute) for which the imaged characters represent a value. Video-digital merge process 142 is described in more detail below with reference to FIG. 4. Template data 144 and its use, when included, are described in more detail below with reference to FIG. 2 and FIG. 4.

Although two analog libraries 110 and associated analog players 120 are shown for purposes of illustration, in other embodiments a system includes fewer or more libraries 110 and analog players 120, but at least one of each. Furthermore, although one patient-encounter information database 150 and one DICOM object database and one A/D converter 130 are shown, in other embodiments, more than one such database is included in a system and hybrid digital objects other than DICOM objects are stored in database 160 instead of or in addition to DICOM objects. Although one local network 180 is shown, in other embodiments more or fewer local networks or one or more wide area networks connect computer 140 to database 150, or database 160, or both. In some embodiments, digital video from video A/D converter 130 is communicated to computer 140 over a network, such as local area network 180. In some embodiments, general purpose computer 140 is replaced by a special purpose computer, and one or more blocks shown as separate units are combined into a single unit. For example, in some embodiments A/D converter 130 and computer 140 are combined.

According to various embodiments of the invention, character data apparent in the images of the video frames is used to automatically associate a digital video clip with non-video descriptive data related to the video clip, and to automatically store a digital video clip in association with the non-video descriptive data in a second database, such as DICOM object database 160.

2. Video Data

The video data processed by system 100 includes images of characters in one or more portions of each frame. A video clip, as is well known, is a series of images, called frames, taken at evenly separated times in rapid succession specified by a frame rate. Typical frame rates are on the order of 1 to 24 frames per second. An analog image represents controls to a cathode ray tube that sweeps across a television screen in interleaved groups of rows at a prescribed rate. The characteristics of the cathode ray that are controlled include intensity for monochrome video (so called "Black and White" video) and include color information, such as hue, for color video. Characters in such video, such as the letter "A" or the numeral "1" are recognizable to a human observer as uniform intensity or color spots on the screen that are positioned to produce character shapes.

Each image in a digital video is composed of indivisible picture elements (pixels) arranged in rows. A typical television image is well represented by 640 pixels in each of 480 rows. One octet (eight binary digits called bits) represents a range of grays from white to black in monochrome digital video. In color digital video, three octets each represent a range of intensities for one of three colors that mix to form one of millions of perceived colors. Characters in such video, such as the letter "A" or the numeral "1" are recognizable to a human observer as uniform intensity or color pixels on the screen that are positioned to produce character shapes.

Non-video digital data are series of values, such as binary octets, that code characters or numbers. A number can be represented directly in binary. Floating point number are a composite of two binary numbers, indicating a fraction and an exponent. Characters, including numerals, are represented indirectly by codes, where a different value represents a different character according to one of several standards, such as the ASCII standard, well known in the art, using binary codes. A series of one or more octets of binary codes may represent a number or a series of characters, depending on how the octets are used by a computer program.

An optical character recognition process is a computer program that examines the pixels in a digital image (such as a video frame) and determines whether the pixels are arranged in such a way as to represent a character. If so, the character so recognized is output by the process as the code for the character. Thus if pixels are arranged to create a yellow capital letter A in a digital image, the optical character recognition process outputs the code for the capital letter A, e.g. the octet "01000001" in the binary ASCII standard. To distinguish characters in images from code for characters, the former is called herein character image data and the latter is called character code data. To distinguish character code data from binary data that represents integers or floating point numbers, the latter is called herein numeric binary data. Note that character code data that represents numerals can be converted to numeric binary data. For example, ASCII characters that represent the numerals "1" followed by "3" (i.e., "00110001" followed by "00110011") can be converted to numeric binary data that represents the number thirteen, i.e., "1101."

According to embodiments of the invention, analog character image data is converted to digital character image data in A/D converter 130; and then is converted in an optical character recognition process within the video-digital merge process 142 to character code data.

It is noted that the meaning of the characters detected in an image depends on the legacy system and possibly on the location of the characters. For example, one legacy system may image characters that represent a patient identifier (patient ID) and another legacy system may image characters that represent instead a case identifier (case ID) that is based on both a doctor and a patient visit. Some legacy systems may also image characters that represent the facility or the date or the time or some combination in addition to the patient ID or case ID or some combination.

Figure 2A:
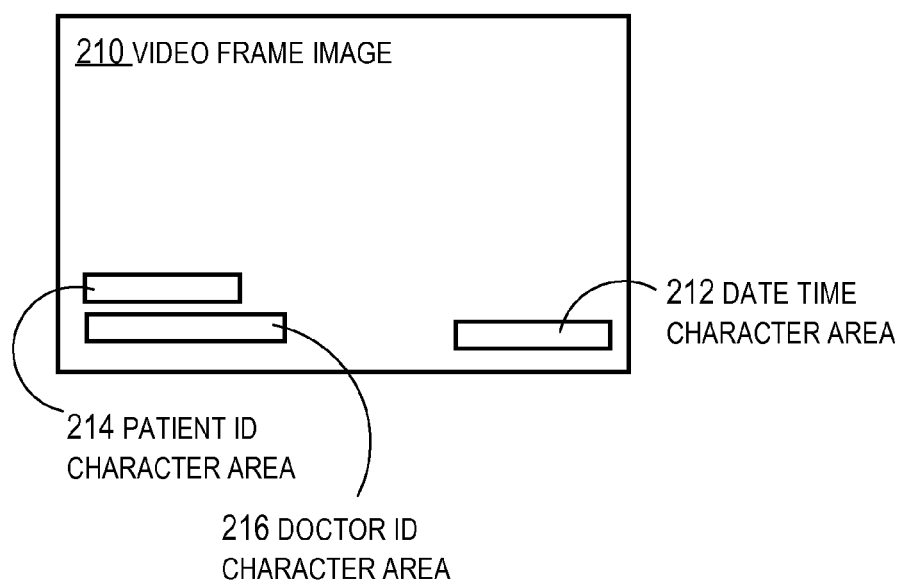
FIG. 2A and FIG. 2B are block diagrams that illustrate different areas for different character data used to identify patient demographic information associated with video data on different example legacy systems.
Figure 2B:
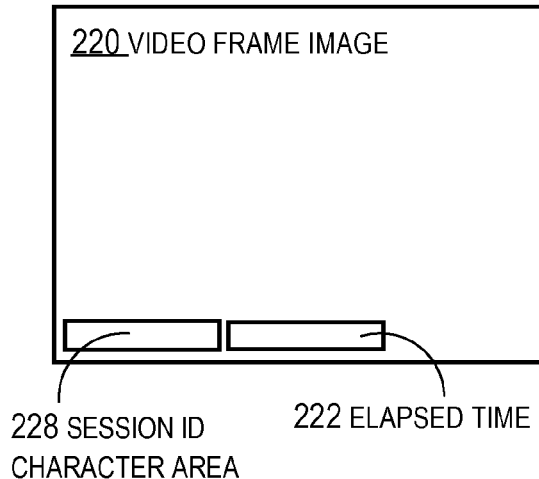

FIG. 2A and FIG. 2B are block diagrams that illustrate different areas for different character data used to identify patient demographic information associated with video data on different example legacy systems.

FIG. 2A is a block diagram that illustrates a video frame 201 of a first legacy system after conversion to digital video. The frame 201 holds an image 210 made up of pixels (not shown) that represent the internal structure of a patient. Superimposed on the representation of the patient's internal structure are locations where the analog image had been changed to represent character image data for one or more attributes. The character image data is found in each of several limited areas 212, 214, 216 of the image 210. In a date-time character area 212, characters indicate the date and time when the frame was recorded. In a patient ID character area 214, characters indicate a patient ID for the patient whose internal structure is represented by the image 210. In a doctor ID character area 216, characters indicate a doctor ID for a doctor who is treating the patient indicated by the patient ID in area 214. In all video collected by the first legacy system, the information for the date and time, patient ID and doctor ID attributes are placed as character image data in the areas 212, 214, 216, respectively. The characters in the areas 212, 214, 216 change, but the context or attribute for those characters remains the same for the first legacy system, e.g., date-time, patient ID, doctor ID.

FIG. 2B is a block diagram that illustrates a video frame 202 of a second legacy system after conversion to digital video. The frame 202 holds an image 220 made up of pixels (not shown) that represent the internal structure of a patient. Superimposed on the representation of the patient's internal structure are locations where the analog image had been changed to represent character image data. The character image data is found in each of several limited areas 222, 228 of the image 210. In elapsed time character area 222, characters indicate the amount of time that passed since the start of the recording. In a encounter identifier (encounter ID) character area 228, characters indicate a encounter ID that is a unique number for a combination of patient and the session with the imaging system that determines the internal structure represented by the image 220. In all video collected by the second legacy system, the information for the elapsed time and encounter ID attributes are placed as character image data in the areas 222 and 228, respectively. The characters in the areas 222, 228 change, but the context or attribute for those characters remains the same for the second legacy system, e.g., elapsed time and encounter ID.

Figure 3:
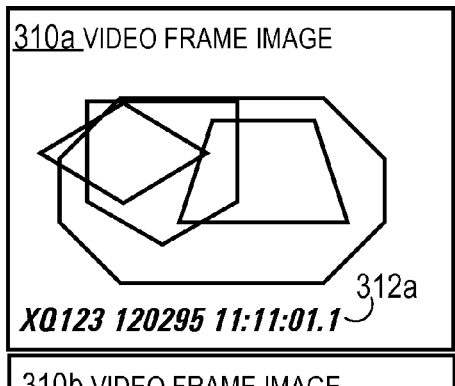
FIG. 3 is a block diagram that illustrates an example boundary between two patient imaging sessions.
Figure 3:
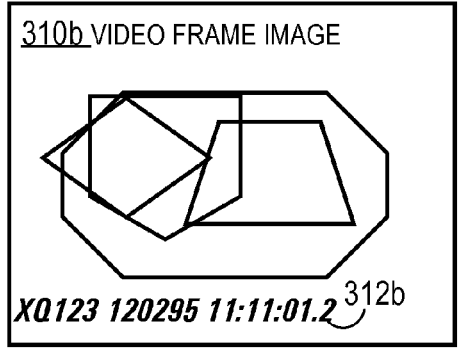
Figure 3:
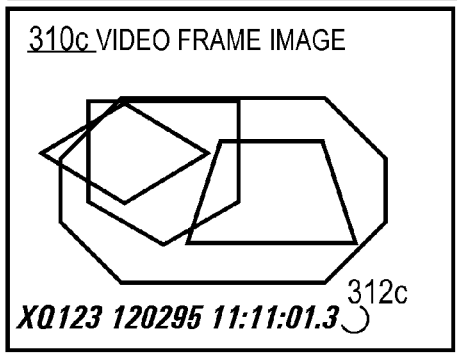
Figure 3:
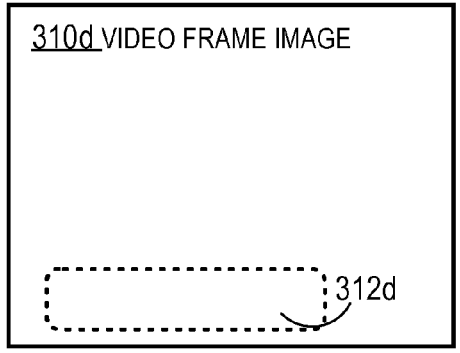
Figure 3:
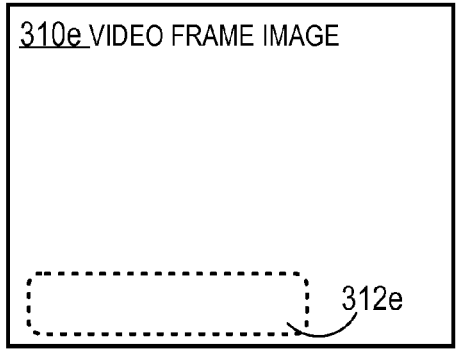
Figure 3:
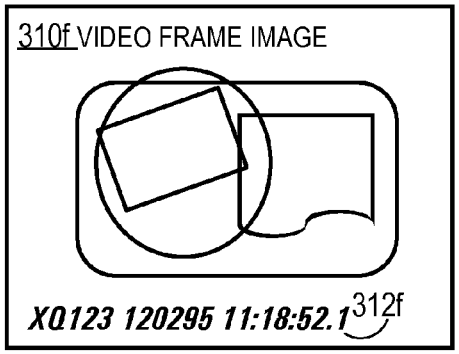
Figure 3:
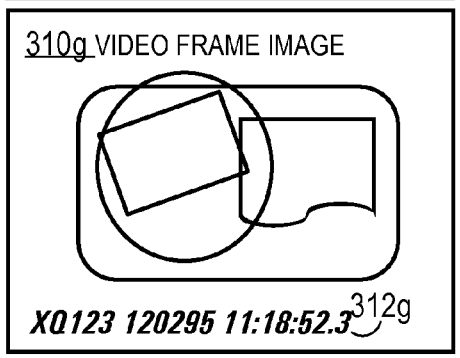
Figure 3:
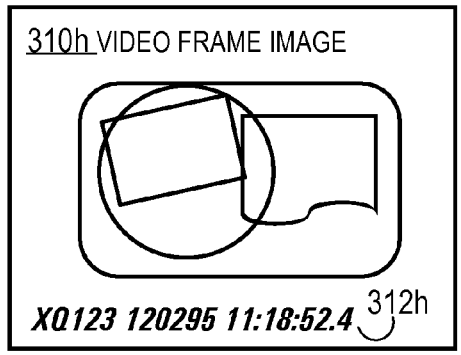

FIG. 3 is a block diagram that illustrates a boundary between two patient imaging sessions in a video frame sequence 300 from an example legacy system. The video sequence 300 includes successive frames (called a video clip). The first frame in the sequence includes a video frame with video frame image data 310*a*, followed by successive frames with video frame image data 310*b*, 310*c*, 310*d*, 310*e*, 310*f*, 310*g* and 310*h*. Video frame image 310*a* includes an octagon, diamond, trapezoid and pentagon that schematically represent the internal structure of a first patient. The image 310*a* also includes character data in area 312*a*. In the illustrated clip 300, the character data indicates a device ID and date and time. Note that the location of the date-time in area 312*a* is different from that shown in FIG. 2A and that no date-time area is shown in FIG. 2B Thus FIG. 3 illustrates a video clip from a third different legacy system.

The successive frames of clip 300 include the video frame images 310*b*, 310*c*, 310*d*, 310*e*, 310*f*, 310*g*, 310*h*, respectively. The date and time, if available, for each frame is shown in areas 312*b*, 312*c*, 312*d*, 312*e*, 312*f*, 312*g*, 312*h*, respectively. Areas 312*a* through 312*h* are collectively referenced hereinafter as character area 312.

The clip 300 depicts a boundary between video data for a first encounter with a first patient and a different encounter with the same or different patient. Images 310*b* and 310*c* belong to the first encounter and are similar to image 310*a*. The size and positions of the polygons representing internal structure change slightly among images 310*a*, 310*b*, 310*c*. Images 310*f*, 310*g*, 310*h* belong to a different second encounter. Video frame image 310*f* includes a rounded-corner rectangle, rotated rectangle, irregular shape and oval that represent the internal structure of the second patient, and that correspond to the octagon, diamond, trapezoid and pentagon that represent the internal structure of a first patient. Between images 310*c* and 310*f* are two images 310*d*, 310*e* without image data indicating internal structure of a patient, such as occurs in a video clip recorded during no input data or during a fade out recording mode.

As described in more detail below, in some embodiments, the changes in image content from image 310*c* to images 310*d*, 310*e* and then to image 310*f* are used to detect the boundary between different patient encounters on an imaging device. Although some particular characteristics of the boundary are shown in FIG. 3 for purposes of illustration, in other embodiments more, fewer or different changes occur at the boundary between imaging sessions of patients.

3. Video-Digital Merge Process

FIG. 4 is a flow diagram that illustrates at a high level a method 400 for converting analog medical video to combined digital data objects, according to an embodiment. Although steps are shown in FIG. 4 in a particular order for purposes of illustration, in other embodiments, the steps may be performed in a different order, or overlapping in time by one or more parallel or serial processes, or some steps may be omitted, or some combination of changes may be involved.

Method 400 includes step 401 that is performed manually in some embodiments and automatically in other embodiments. Method 400 also includes step 408 that is performed by analog player (e.g., player 120) and A/D converter (e.g., A/D converter 130). Method 400 also includes steps 410 through 490 that are performed by the video-digital merge process (e.g., process 142) on one or more processors, such as one or more processors on computer 140.

In step 410, legacy template data (e.g., data 144 on computer 140) is received that indicates the location of character areas on a video frame and the context or attribute for those characters for each legacy system of interest. For example, template data is received for three legacy systems. The example template data indicates that in the first legacy system the character areas 212, 214, 216 are used for date-time, patient ID and doctor ID, respectively. The example template data indicates that in the second legacy system the character areas 222, 228 are used for elapsed time and encounter ID, respectively. The example template data also indicates that in the third legacy system the character area 312 is used for device ID and date and time, in that order.

Any method may be used to receive the template data. In various embodiments, the template data is predefined and stored within source code or in files stored with the executable code or in files or a database accessible to the merge process. In some embodiments, the data is received at the time of execution, such as when input manually or when received in a message from a different local or remote process either in response to a prompt or query message, or unsolicited.

In an illustrated embodiment, step 401 is performed manually by a human operator and includes steps 402 and 404. In step 402 a legacy system library is selected and indicated to the merge process, for example by selecting options from a graphical user interface on computer 140 or remotely on a computer connected to local area network 180.

In step 404, a medium from the library for the legacy system selected in step 401 is inserted into an analog video player compatible with the legacy system. For example medium 112 is taken from library 110a and inserted into player 120a.

In some embodiments, step 401 is performed by an automated system that controls a robotic arm. The controller causes the robotic arm to select a medium from a library and insert the medium into an appropriate player. In some of these embodiments, the controller selects the medium according to a program, such as a program to go in order through every tape in a library. In some of these embodiments, the controller indicates the legacy system from which media are being loaded to the merge process (e.g., process 142 on computer 140).

In step 408 the analog video output from the player (e.g., player 120a) is input to the video A/D converter (e.g., converter 130). This can be done in any way. For example, a cable from player 120a is connected to an input port of A/D converter 130 in some embodiments. In some embodiments, a switch that connects both players 120a and 120b to A/D converter 130 is thrown to cause output from player 120a to feed into A/D converter 130. The switch may be internal to A/D converter 130 or external (not shown). In some embodiments, connections are hardwired and step 408 is omitted.

In step 412, legacy data that indicates the legacy system that is the source of the analog data is received at the merge process. In various embodiments, the legacy data is received in response to step 402 performed manually or automatically by a controller for a robotic arm. For example, data is received at merge process 142 that indicates the legacy system is the third legacy system that produces video like that shown in FIG. 3.

In step 420, digital video is received at the merge process (e.g., process 142 on computer 140). For example, the video clip shown in FIG. 3 is received by process 142.

In step 430, character code data is produced based on the digital video received in step 420. In the illustrated embodiment, step 430 includes determining the portion of the image of the current frame that holds character data based on the template data and the legacy data. For example, merge process 142 determines from the legacy data that the third legacy system is the source of the video. The merge process then determines from template data 144 that the third legacy system uses area 312 to report the device and date and time that recorded the video. The area 312 is fed into a video optical character recognition (video OCR) process to output character code data for the sequence of characters found in area 312. Any OCR known in the art may be used to generate character code data from the character image data in the image area of interest, e.g. area 312.

In step 440, non-video descriptive data for the video clip is determined based on the character code data. In some embodiments, the descriptive data is the same as the character code data. For example, in some embodiments, the device ID "XQ123" and the start date "12/02/1995" and time "11:18:52.1" of the first image 310f for the session is used as the descriptive data. In some embodiments, data based on the character code data is used as the descriptive data. For example, procedure duration is non-video descriptive data derived from the difference between the time of the first frame and the time of the last frame for the session.

In some embodiments, step 440 includes retrieving data from a database (e.g., patient encounter database 150) based on the character code data. For example, the date and device is used in an SQL query to database 150 to find a patient encounter record that used that device at that time. Then other information from that record is retrieved as non-video descriptive data. For example, based on device ID XQ123, date 12/02/95 and time 11:18:52.1, patient demographic data and test demographic data are retrieved from database 150. Patient demographic data describes the patient and the population of which the patient is a member, such as the patient's age, height, weight, race, zip code, insurance type, among others. The database may also include patient particular data, such as name, ID, social security number, address, telephone number, insurer, among others. Study demographics describe the measurement group, such as disease, treatment, population size, study duration, study start date, among others.

In some embodiments, the character code data indicates a primary index into the database 150. For example, in some embodiments, the character code data retrieved from the encounter ID character area 228 for the second legacy system is also an index into a Radiology Information System (RIS) database.

In step 450, the digital video data is stored in association with the descriptive data in a database (e.g., DICOM database 160). In some embodiments, step 450 involves storing the digital video data on database 160 along with a pointer to one or more records in database 150. In the illustrated embodiment, step 450 comprises forming a DICOM object that includes the digital video for the session in a "CINE" field along with binary data for characters and numbers retrieved from the RIS 150 in one or more other fields to indicate non-video descriptive data associated with the video data (often called metadata, i.e., data about data); and storing the composite DICOM object in database 160.

In step 460 a boundary between the current patient session video data and a different patient session video data is determined. Any method may be used. In some embodiments, a set of one or more frames with no image data is determined to be a boundary. For example, images 310d, 310e of clip 300 are determined to have no image data and therefore serve as a boundary between a first session and a second session.

In some embodiments, the first image after the no image frame or frames is compared to the last image before the no image frame or frames. A measure of similarity between the two images is determined. Any measure of similarity may be used. For example, a correlation between the two images is determined. If the measure of similarity is above some threshold, the two images are judged to belong to the same patient session. In such a case, any intervening frames without image data will not be considered a boundary between two sessions. If the measure of similarity is below that threshold, then one of the intervening frames without image data is considered a boundary.

In some embodiments, there are not frames without image data between sessions. In such embodiments, the measure of similarity can be used to determine a boundary. For example, a measure of similarity among images 310*a* to 310*c* is greater than a measure of similarity between images 310*c* and 310*f*. Therefore, the frame of image 310*f* is judged to start a different session in some embodiments.

In some embodiments, a large change in any character code data determined from successive frames can be used to determine a boundary between sessions. For example, the time difference among successive images 310*a*, 310*b*, 310*c* is about 0.1 seconds; but the time difference between image 310*c* and image 310*f* is more than eight minutes. Therefore, in some embodiments it is judged that a session boundary occurs between the frame of image 310*c* and the frame of image 310*f*.

Control then passes to step 490. In step 490 it is determined whether the end of data on the medium has been reached. If so, control passes to step 404 to insert another medium into the analog player. If it is determined in step 490 that there is more data on the current medium, then control passes to step 430 to determine the character code data for the next session on the current medium.

In some embodiments, in which all analog data to be converted use the same legacy system or several systems are all compatible with the same legacy system in terms of video media and location and context of character areas, steps 402, 410 and 412 can be omitted. The system 100 is set up at one time and takes all character image data from the same area of each frame and interprets the resulting character code data in the same context or as the same attribute.

In some embodiments, the medium play rate in step 404 and processing during steps 420 through 490 are performed at faster than real time.

Using the steps of method 400 with the apparatus of system 100, large libraries of analog video data from legacy systems can be converted to digital objects with little or no human involvement. This saves the cost of human salaries and the cost of human errors and the cost of delays between the request and the viewing of the data. When data is desired after conversion, it is retrieved immediately over network 180 from DICOM OBJECT database 4. Computer Hardware Overview FIG. 5 is a block diagram that illustrates a computer system 500 upon which an embodiment of the invention may be implemented. Computer system 500 includes a communication mechanism such as a bus 510 for passing information between other internal and external components of the computer system 500. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). A sequence of binary digits constitutes digital data that is used to represent a number or code for a character. A bus 510 includes many parallel conductors of information so that information is transferred quickly among devices coupled to the bus 510. One or more processors 502 for processing information are coupled with the bus 510. A processor 502 performs a set of operations on information. The set of operations include bringing information in from the bus 510 and placing information on the bus 510. The set of operations also typically include comparing two or more units of information, shifting positions of units of information, and combining two or more units of information, such as by addition or multiplication. A sequence of operations to be executed by the processor 502 constitute computer instructions.

Computer system 500 also includes a memory 504 coupled to bus 510. The memory 504, such as a random access memory (RAM) or other dynamic storage device, stores information including computer instructions. Dynamic memory allows information stored therein to be changed by the computer system 500. RAM allows a unit of information stored at a location called a memory address to be stored and retrieved independently of information at neighboring addresses. The memory 504 is also used by the processor 502 to store temporary values during execution of computer instructions. The computer system 500 also includes a read only memory (ROM) 506 or other static storage device coupled to the bus 510 for storing static information, including instructions, that is not changed by the computer system 500. Also coupled to bus 510 is a non-volatile (persistent) storage device 508, such as a magnetic disk or optical disk, for storing information, including instructions, that persists even when the computer system 500 is turned off or otherwise loses power.

Information, including instructions, is provided to the bus 510 for use by the processor from an external input device 512, such as a keyboard containing alphanumeric keys operated by a human user, or a sensor. A sensor detects conditions in its vicinity and transforms those detections into signals compatible with the signals used to represent information in computer system 500. Other external devices coupled to bus 510, used primarily for interacting with humans, include a display device 514, such as a cathode ray tube (CRT) or a liquid crystal display (LCD), for presenting images, and a pointing device 516, such as a mouse or a trackball or cursor direction keys, for controlling a position of a small cursor image presented on the display 514 and issuing commands associated with graphical elements presented on the display 514.

In the illustrated embodiment, special purpose hardware, such as an application specific integrated circuit (IC) 520, is coupled to bus 510. The special purpose hardware is configured to perform operations not performed by processor 502 quickly enough for special purposes. Examples of application specific ICs include graphics accelerator cards for generating images for display 514, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 500 also includes one or more instances of a communications interface 570 coupled to bus 510. Communication interface 570 provides a two-way communication coupling to a variety of external devices that operate with their own processors, such as printers, scanners and external disks. In general the coupling is with a network link 578 that is connected to a local network 580 to which a variety of external devices with their own processors are connected. For example, communication interface 570 may be a parallel port or a serial port or a universal serial bus (USB) port on a personal computer. In some embodiments, communications interface 570 is an integrated services digital network (ISDN)

card or a digital subscriber line (DSL) card or a telephone modem that provides an information communication connection to a corresponding type of telephone line. In some embodiments, a communication interface 570 is a cable modem that converts signals on bus 510 into signals for a communication connection over a coaxial cable or into optical signals for a communication connection over a fiber optic cable. As another example, communications interface 570 may be a local area network (LAN) card to provide a data communication connection to a compatible LAN, such as Ethernet. Wireless links may also be implemented. For wireless links, the communications interface 570 sends and receives electrical, acoustic or electromagnetic signals, including infrared and optical signals, that carry information streams, such as digital data. Such signals are examples of carrier waves.

The term computer-readable medium is used herein to refer to any medium that participates in providing information to processor 502, including instructions for execution. Such a medium may take many forms, including, but not limited to, non-volatile media, volatile media and transmission media. Non-volatile media include, for example, optical or magnetic disks, such as storage device 508. Volatile media include, for example, dynamic memory 504. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 578 typically provides information communication through one or more networks to other devices that use or process the information. For example, network link 578 may provide a connection through local network 580 to a host computer 582 or to equipment 584 operated by an Internet Service Provider (ISP). ISP equipment 584 in turn provides data communication services through the public, world-wide packet-switching communication network of networks now commonly referred to as the Internet 590. A computer called a server 592 connected to the Internet provides a service in response to information received over the Internet. For example, server 592 provides information representing video data for presentation at display 514.

The invention is related to the use of computer system 500 for implementing the techniques described herein. According to one embodiment of the invention, those techniques are performed by computer system 500 in response to processor 502 executing one or more sequences of one or more instructions contained in memory 504. Such instructions, also called software and program code, may be read into memory 504 from another computer-readable medium such as storage device 508. Execution of the sequences of instructions contained in memory 504 causes processor 502 to perform the method steps described herein. In alternative embodiments, hardware, such as application specific integrated circuit 520, may be used in place of or in combination with software to implement the invention. Thus, embodiments of the invention are not limited to any specific combination of hardware and software.

The signals transmitted over network link 578 and other networks through communications interface 570, which carry information to and from computer system 500, are exemplary forms of carrier waves. Computer system 500 can send and receive information, including program code, through the networks 580, 590 among others, through network link 578 and communications interface 570. In an example using the Internet 590, a server 592 transmits program code for a particular application, requested by a message sent from computer 500, through Internet 590, ISP equipment 584, local network 580 and communications interface 570. The received code may be executed by processor 502 as it is received, or may be stored in storage device 508 or other non-volatile storage for later execution, or both. In this manner, computer system 500 may obtain application program code in the form of a carrier wave.

Various forms of computer readable media may be involved in carrying one or more sequence of instructions or data or both to processor 502 for execution. For example, instructions and data may initially be carried on a magnetic disk of a remote computer such as host 582. The remote computer loads the instructions and data into its dynamic memory and sends the instructions and data over a telephone line using a modem. A modem local to the computer system 500 receives the instructions and data on a telephone line and uses an infra-red transmitter to convert the instructions and data to an infra-red signal, a carrier wave serving as the network link 578. An infrared detector serving as communications interface 570 receives the instructions and data carried in the infrared signal and places information representing the instructions and data onto bus 510. Bus 510 carries the information to memory 504 from which processor 502 retrieves and executes the instructions using some of the data sent with the instructions. The instructions and data received in memory 504 may optionally be stored on storage device 508, either before or after execution by the processor 502.

5. Extensions and Alternatives

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for converting analog medical video data to digital objects, comprising the steps of:
   a. receiving a digital video signal produced by converting an analog video signal received in response to playing a recording of analog medical video associated with a legacy system on an analog video player compatible with the legacy system;
   b. determining without human intervention a first portion of a video frame of the digital video signal where characters are imaged onto the analog medical video by the legacy system, wherein the first portion is associated with a particular context for the legacy system;
   c. processing the first portion of the video frame in a video optical character recognition process to generate first character code data;
   d. determining without human intervention non-video descriptive data associated with the analog medical video data based on the first character code data and the particular context; and e. storing without human intervention digital video data based on the digital video signal in association with the non-video descriptive data.

2. A method as recited in claim 1, wherein:
the method further comprises
receiving legacy template data that associates a plurality of portions of a video frame with a corresponding plurality of different legacy systems, and
receiving legacy type data that indicates among the plurality of different legacy systems a particular legacy system that stored the analog medical video data; and
said step of determining the first portion of the video frame further comprises determining the first portion of the video frame based on the legacy type data and the legacy template data.

3. A method as recited in claim 1, wherein:
said step of determining the first portion of the video frame further comprises determining the first portion of the video frame where characters are imaged to indicate an index into a database of patient encounter information; and
said step of determining non-video descriptive data associated with the analog medical video data further comprising retrieving the non-video descriptive data from the database of patient encounter information based on the index into the database.

4. A method as recited in claim 1, said step of storing digital video data based on the digital video signal further comprising the step of storing the digital video data and the non-video descriptive data together in a single Digital Imaging and Communications in Medicine (DICOM) object.

5. A method as recited in claim 1, further comprising determining without human intervention a boundary in the digital video signal between first video data collected for a first imaging session with a first patient and different video data collected for a different second imaging session with a second patient.

6. A method as recited in claim 5, further comprising repeating steps b, c, d and e for the different video data collected for the different second imaging session with the second patient.

7. A method as recited in claim 5, wherein the second patient is the same as the first patient.

8. A method as recited in claim 1, wherein the non-video descriptive data includes at least one of patient identifier, encounter identifier, procedure type, date of procedure, start time of procedure, duration of procedure, imaging device identifier, or identifier for imaging device operator.

9. A non-transitory computer-readable medium carrying one or more sequences of instructions for converting analog medical video data to digital objects, wherein execution of the one or more sequences of instructions by one or more processors causes the one or more processors to perform the steps of:
a. receiving a digital video signal produced by converting an analog video signal received in response to playing a recording of analog medical video associated with a legacy system on an analog video player compatible with the legacy system;
b. determining a first portion of a video frame of the digital video signal where characters are imaged onto the analog medical video by the legacy system, wherein the first portion is associated with a particular context for the legacy system;
c. processing the first portion of the video frame in a video optical character recognition process to generate first character code data;
d. determining non-video descriptive data associated with the analog medical video data based on the first character code data and the particular context; and
e. storing digital video data based on the digital video signal in association with the non-video descriptive data.

10. A computer-readable medium as recited in claim 9, wherein:
execution of the one or more sequences of instructions further causes the one or more processors to perform the steps of
receiving legacy template data that associates a plurality of portions of a video frame with a corresponding plurality of different legacy systems, and
receiving legacy type data that indicates among the plurality of different legacy systems a particular legacy system that stored the analog medical video data; and
said step of determining the first portion of the video frame further comprises determining the first portion of the video frame based on the legacy type data and the legacy template data.

11. A computer-readable medium as recited in claim 9, wherein:
said step of determining the first portion of the video frame further comprises determining the first portion of the video frame where characters are imaged to indicate an index into a database of patient encounter information; and
said step of determining non-video descriptive data associated with the analog medical video data further comprising retrieving the non-video descriptive data from the database of patient encounter information based on the index into the database.

12. A computer-readable medium as recited in claim 9, said step of storing digital video data based on the digital video signal further comprising the step of storing the digital video data and the non-video descriptive data together in a single Digital Imaging and Communications in Medicine (DICOM) object.

13. A computer-readable medium as recited in claim 9, wherein execution of the one or more sequences of instructions further causes the one or more processors to perform the step of determining without human intervention a boundary in the digital video signal between first video data collected for a first imaging session with a first patient and different video data collected for a different second imaging session with a second patient.

14. A computer-readable medium as recited in claim 13, wherein execution of the one or more sequences of instructions further causes the one or more processors to perform the steps of repeating steps b, c, d and e for the different video data collected for the different second imaging session with the second patient.

15. A computer-readable medium d as recited in claim 13, wherein the second patient is the same as the first patient.

16. A computer-readable medium as recited in claim 9, wherein the non-video descriptive data includes at least one of patient identifier, encounter identifier, procedure type, date of procedure, start time of procedure, duration of procedure, imaging device identifier, or identifier for imaging device operator.

17. A system for converting analog medical video data to digital objects comprising:
a video analog to digital converter;
one or more computer-readable media;
one or more processors; and
one or more sequences of instructions stored on the one or more computer-readable media, wherein execution of the one or more sequences of instructions by the one or more processors causes the one or more processors to perform the steps of:

receiving from the video analog to digital converter a digital video signal produced by converting an analog video signal received in response to playing a recording of analog medical video associated with a legacy system on an analog video player compatible with the legacy system;

determining a first portion of a video frame of the digital video signal where characters are imaged onto the analog medical video by the legacy system, wherein the first portion is associated with a particular context for the legacy system;

processing the first portion of the video frame in a video optical character recognition process to generate first character code data;

determining non-video descriptive data associated with the analog medical video data based on the first character code data and the particular context; and storing, on the one or more computer-readable media, digital video data based on the digital video signal in association with the non-video descriptive data.

18. A system as recited in claim 17, further comprising the analog video player compatible with the legacy system.

19. A system as recited in claim 18, further comprising an automated media retrieval system for retrieving without human intervention media that holds the recording of analog medical video associated with the legacy system and inserting the media into the analog video player.

20. A system as recited in claim 17, wherein:

said step of determining the first portion of the video frame further comprises determining the first portion of the video frame where characters are imaged to indicate an index into a database of patient encounter information; and said step of determining non-video descriptive data associated with the analog medical video data further comprising retrieving the non-video descriptive data from the database of patient encounter information based on the index into the database.

* * * * *